United States Patent
Rolando et al.

(10) Patent No.: US 6,309,414 B1
(45) Date of Patent: *Oct. 30, 2001

(54) ANGIOPLASTY STENTS

(75) Inventors: Giovanni Rolando, Chivaso; Paolo Gaschino, Chivasso; Franco Vallana, Turin; Osvaldo Cerise, Aosta, all of (IT)

(73) Assignee: Sorin Biomedica Cardio S.p.A. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/964,158

(22) Filed: Nov. 4, 1997

(51) Int. Cl.$^7$ ........................................................ A61F 2/06
(52) U.S. Cl. ............................................. 623/1.15; 623/1.3
(58) Field of Search .................................. 623/1, 11, 12, 623/1.15, 1.16, 1.18, 1.3, 1.14, 1.17, 2; 600/37; 606/194, 195

(56) References Cited

U.S. PATENT DOCUMENTS

| 4,503,569 | 3/1985 | Dotter . |
| 4,768,507 | 9/1988 | Fischell et al. . |

(List continued on next page.)

FOREIGN PATENT DOCUMENTS

| 297 01 758 U1 | 5/1997 | (DE) . |
| 297 02 671 U1 | 5/1997 | (DE) . |
| 0 540 290 A2 | 10/1992 | (EP) . |
| 0 887 051 A1 | 12/1998 | (EP) . |
| WO 96/03092 A1 | 2/1996 | (WO) . |
| WO 9603092 A1 | 2/1996 | (WO) . |
| WO 98/22159 | 5/1998 | (WO) . |
| WO 98/30172 | 7/1998 | (WO) . |
| WO 98/58600 | 12/1998 | (WO) . |
| WO 99/15108 | 4/1999 | (WO) . |
| WO 99/16387 | 4/1999 | (WO) . |
| WO 00/02502 | 1/2000 | (WO) . |
| WO 00/06051 | 2/2000 | (WO) . |

OTHER PUBLICATIONS

European Search Report on European Patent Application No. EP 98 10 7382, including annex, dated Sep. 7, 1998, 3 pages.

English language abstract of Italian Patent Application No. TO96A000655.

Topol, *Textbook of Interventional Cardiology*, 2(2):687–815 (1994).

*Primary Examiner*—David H. Willse
*Assistant Examiner*—Suzette J. Jackson
(74) *Attorney, Agent, or Firm*—Popovich & Wiles, P.A.

(57) ABSTRACT

An angioplasty stent comprises a body comprising a plurality of successive segments connected in pairs by bridge means so that the successive segments can be oriented relative to one another for the purposes of bending of the body in any direction defined by a linear combination of respective orientation axes defined by the bridge connection means. During the radial expansion of the stent, the axial contraction of the segments resulting from the opening-out of the respective loops is compensated by axial projection of the bridge elements from the respective concave portions. The wall of the body comprises arms for supporting a lumen as well as regions which are selectively deformable during the expansion of the stent, the arms and the selectively deformable regions having different cross-sections and/or cross-sectional areas. At least one portion of the body may have a substantially reticular structure, the branches of which define geometrical figures identifiable as fractals.

21 Claims, 6 Drawing Sheets

U.S. PATENT DOCUMENTS

| | | | |
|---|---|---|---|
| 4,776,337 | 10/1988 | Palmaz | 623/1 |
| 4,800,882 | 1/1989 | Gianturco | 623/13 |
| 4,830,003 | 5/1989 | Wolff et al. | 623/1 |
| 4,856,516 | 8/1989 | Hillstead | 623/12 |
| 4,886,062 | 12/1989 | Wiktor | 623/1 |
| 4,907,336 | 3/1990 | Gianturco . | |
| 5,383,892 * | 1/1995 | Cardon et al. | 606/198 |
| 5,421,955 | 6/1995 | Lau et al. . | |
| 5,449,373 | 9/1995 | Pinchasik et al. . | |
| 5,514,154 * | 5/1996 | Lau et al. | 606/194 |
| 5,569,295 | 10/1996 | Lam . | |
| 5,591,197 | 1/1997 | Orth et al. . | |
| 5,603,721 | 2/1997 | Lau et al. . | |
| 5,630,829 * | 5/1997 | Lauterjung | 623/1.15 |
| 5,649,952 | 7/1997 | Lam . | |
| 5,681,346 | 10/1997 | Orth et al. . | |
| 5,695,516 * | 12/1997 | Fischell et al. | 606/198 |
| 5,697,971 | 12/1997 | Fischell et al. . | |
| 5,718,713 | 2/1998 | Frantzen . | |
| 5,725,548 * | 3/1998 | Jayaraman | 623/1.15 |
| 5,725,572 | 3/1998 | Lam et al. . | |
| 5,728,131 | 3/1998 | Frantzen et al. . | |
| 5,728,158 | 3/1998 | Lau et al. . | |
| 5,733,303 * | 3/1998 | Israel et al. | 606/198 |
| 5,733,330 | 3/1998 | Cox . | |
| 5,735,893 | 4/1998 | Lau et al. . | |
| 5,741,327 | 4/1998 | Frantzen . | |
| 5,755,776 * | 5/1998 | Al-Saadon | 623/1 |
| 5,759,174 | 6/1998 | Fischell et al. . | |
| 5,759,192 | 6/1998 | Saunders . | |
| 5,766,238 | 6/1998 | Lau et al. . | |
| 5,766,239 | 6/1998 | Cox . | |
| 5,769,887 | 6/1998 | Brown et al. . | |
| 5,776,161 | 7/1998 | Globerman . | |
| 5,776,181 * | 7/1998 | Lee et al. | 623/1 |
| 5,776,183 | 7/1998 | Kanesaka et al. . | |
| 5,836,964 * | 11/1998 | Richter et al. | 606/194 |
| 5,843,120 * | 12/1998 | Israel et al. | 606/198 |
| 5,913,895 | 6/1999 | Burpee et al. . | |
| 5,938,697 | 8/1999 | Killion et al. . | |
| 6,027,526 | 2/2000 | Limon et al. . | |
| 6,033,433 | 3/2000 | Ehr et al. . | |

* cited by examiner

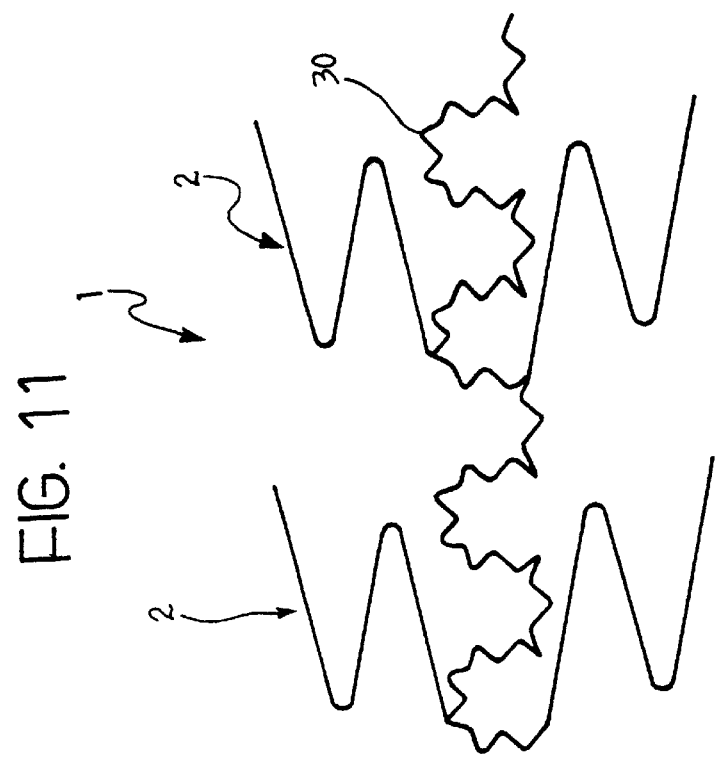
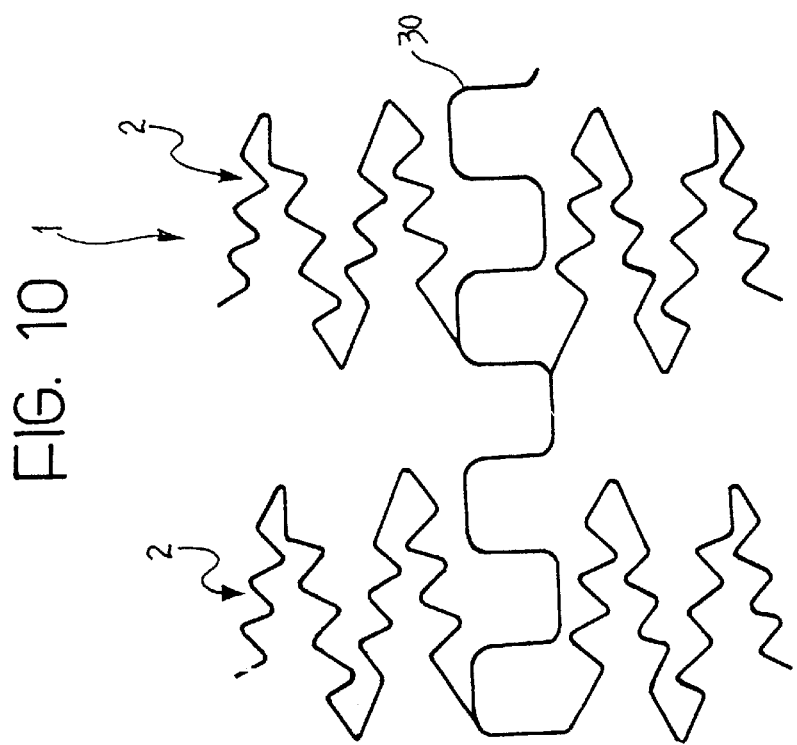

ANGIOPLASTY STENTS

FIELD OF THE INVENTION

The present invention relates in general to so-called stents for angioplasty.

BACKGROUND OF THE INVENTION

The term "stent" is intended to indicate in general a device to be fitted in a lumen (for example, inside a blood vessel), usually by catheterization, and subsequently spread out in situ in order to support the lumen locally. This has the main purpose of preventing the re-establishment of a stenotic site in the location treated. It should, however, be pointed out that it has already been proposed in the art to use substantially similar structures for spreading-out and anchoring vascular grafts in situ; naturally this possible extension of the field of application is also intended to be included in the scope of the invention.

For a general teaching with regard to vascular stents, reference may usefully be made to the work "Textbook of Interventional Cardiology" by Eric J. Topol, W. B. Saunders Company, 1994 and, in particular, to Section IV of Vol. II, entitled "Coronary stenting".

A large number of patent documents are also dedicated to the subject as is shown, for example, by U.S. Pat. No. 4,776,337, U.S. Pat. No. 4,800,882, U.S. Pat. No. 4,907,336, U.S. Pat. No. 4,886,062, U.S. Pat. No. 4,830,003, U.S. Pat. No. 4,856,516, U.S. Pat. No. 4,768,507, and U.S. Pat. No. 4,503,569.

In spite of extensive research and experimentation as documented at the patent level, only a very small number of operative solutions has up to now been used in practice.

This fact can be attributed to various factors, amongst which the following problems or requirements may be mentioned:

- to ensure that, during its advance towards the site to be treated, the stent can adapt in a sufficiently flexible manner to the path along which it is travelling even with regard to portions having small radii of curvature such as those which may be encountered, for example, in some peripheral vessels; this must be achieved without adversely affecting the ability of the stent to perform an effective supporting action once positioned and spread out,
- to prevent, or at least limit the effect of longitudinal shortening which occurs in many stents when they are spread out,
- to offer as broad as possible a bearing surface to the wall of the lumen to be supported,
- to avoid giving rise to complex geometry and/or to possible stagnation sites which, particularly in applications in blood vessels, may give rise to adverse phenomena such as coagulation, clotting, etc., and
- to reconcile the requirements set out above with simple and reliable production methods and criteria, within the scope of currently available technology.

SUMMARY OF THE INVENTION

The object of the present invention, which has the specific characteristics claimed in the following claims, is to solve at least some of the problems outlined above.

In one aspect, this invention is an angioplasty stent comprising a body which has a generally tubular envelope and can be expanded in use from a radially contracted condition towards a radially expanded condition, said body comprising a plurality of successive segments connected in pairs by bridge means, each of the bridge means defining a connecting relationship between two of the segments with a capability for relative orientation identified by at least one respective orientation axis, so that the successive segments can be oriented relative to one another for the purposes of bending of the body in any direction defined by a linear combination of respective orientation axes defined by the bridge connection means.

In another aspect, this invention is an angioplasty stent comprising a body which has a generally tubular envelope and can be expanded in use from a radially contracted condition towards a radially expanded condition, wherein:

the body comprises a plurality of generally annular segments, the wall of each segment being defined by a plurality of loops, and at least some of the segments are interconnected by bridge elements extending in the general direction of the longitudinal axis of the stent and having at least one end connected to the concave or inside portion of a respective loop so that, during the radial expansion of the stent, the axial contraction of the segments resulting from the opening-out of the respective loops is compensated by axial projection of the bridge elements from the respective concave portions.

In another aspect, this invention is an angioplasty stent comprising a body which has a generally tubular envelope and can be expanded in use from a radially contracted position towards a radially expanded condition in which the stent supports the wall of a lumen, wherein the wall of the body comprises arms for supporting the lumen, as well as regions which are selectively deformable during the expansion of the stent, and in that the arms and the selectively deformable regions have different cross-sections and/or cross-sectional areas.

In yet another aspect, this invention is an angioplasty stent comprising a body which has a generally tubular envelope and can be expanded in use from a radially contracted condition towards a radially expanded condition, wherein:

the body comprises a plurality of successive radially expandable segments interconnected by bridge elements extending substantially in the direction of the longitudinal axis of the stent so that the bridge elements are substantially unaffected by the radial expansion of the segments and the bridge elements are generally deformable in the direction of the longitudinal axis so that the length of the stent along the axis can change substantially independently of the radial expansion.

And in yet another aspect, this invention is an angioplasty stent comprising a body which has a generally tubular envelope and can be expanded in use from a radially contracted condition towards a radially expanded condition, wherein at least one portion of the body has a substantially reticular structure, the branches of which define geometrical figures identifiable as fractals.

BRIEF DESCRIPTION OF THE DRAWINGS

The invention will now be described, purely by way of non-limiting example, with reference to the appended drawings, in which.

DETAILED DESCRIPTION OF THE PREFERRED EMBODIMENTS

Figure 1:
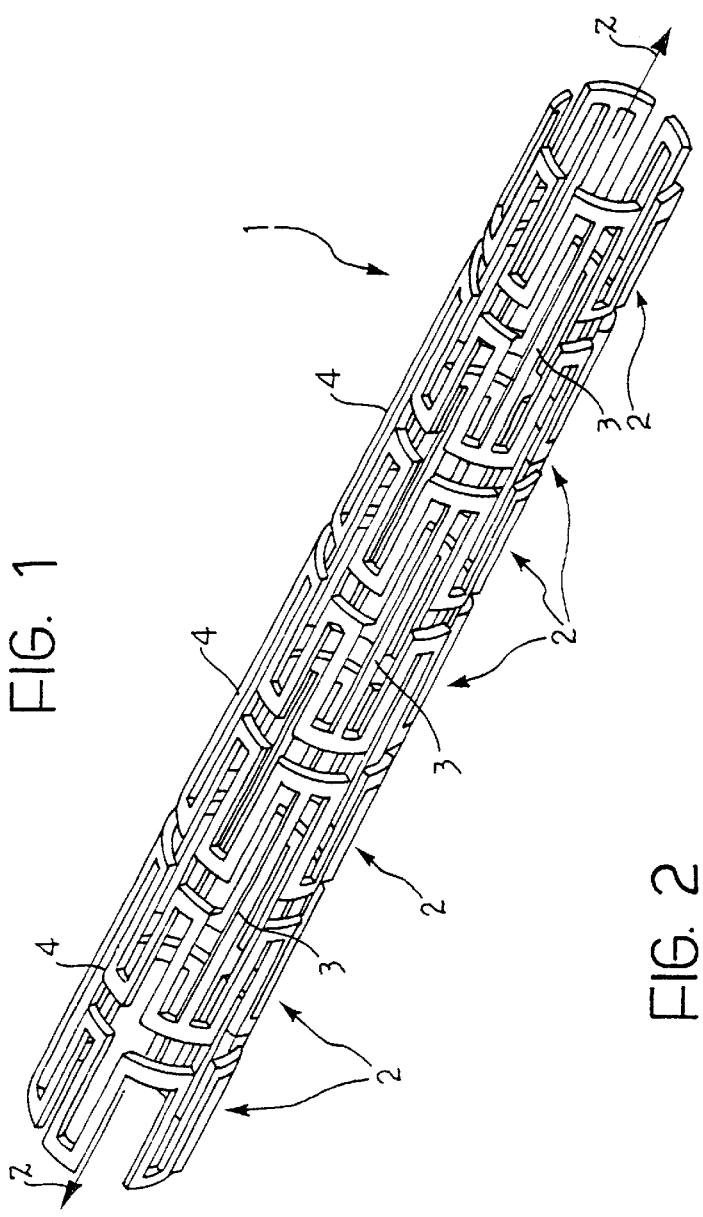
FIG. 1 is a general perspective view of a first angioplasty stent formed in accordance with the invention.

Although several variants are referred to, the reference numeral 1 is used for generally indicating a so-called angioplasty stent FIGS. 1, 2, 7 and 8.

For a general identification of the method of use and the structural characteristics of an implant of this type, reference should be made to the documentation cited in the introductory part of the description.

In summary, it will be remembered that the stent 1 is usually produced in the form of a body with a tubular envelope having an overall length of between a few millimeters and a few tenths of a millimeter, a wall thickness (the wall usually having a mesh or loop structure with openings, as will be explained further below) of the order, for example, of a few hundredths of a millimeter, in view of its possible insertion in a lumen (such as a blood vessel) in a site in which a stenosis is to be remedied. The stent is normally put in position by catheterization, after which radial expansion from an insertion diameter of the order, for example of 1.5–1.8 mm to an expanded diameter, for example, of the order of 3–4 mm takes place in a manner such that, in the expanded condition, the stent supports the lumen, preventing the recurrence of a stenosis. In general, the outside diameter in the radially contracted condition is selected so as to allow the stent to be introduced into the lumen being treated, whereas the expanded diameter corresponds in general to the diameter to be maintained and established in the lumen once the stenosis has been eliminated. It should again be pointed out that, although the main application of the stents described relates to the treatment of blood vessels, its use as an element for supporting any lumen in a human or animal body can certainly be envisaged (and is therefore included within the scope of the invention).

With regard to the methods and criteria which enable the stent to be spread out (that is, expanded in situ), the solution which is currently most widespread is that of the use of a so-called balloon catheter, the stent being disposed around the balloon of the catheter in the contracted condition and the balloon then being expanded once the stent has been brought to the site in which it is to be positioned. However, other solutions are possible, for example, the use of super-elastic materials which cause the stent to expand once the restraining elements, which are intended to keep the stent in the contracted condition until the implant site has been reached, are removed. In addition or alternatively, the use of materials having so-called "shape memory" to form the stent so as to achieve the radial expansion in the implant position has also been proposed.

Usually (for more precise indications, reference should be made to the bibliographical and patent documentation cited in the introduction to the description) the stent is made of metal which can reconcile two basic requirements for the application, that is, plastic deformability during the expansion stage and the ability to withstand any stresses which would tend to cause the stent to close up, preserving the expanded shape. The material known by the trade name of "Nitinol" is well known and also has super-elasticity and shape-memory properties which may be required in the expansion stage.

In any case, these technological aspects will not be dealt with in detail in the present description since they are not relevant per se for the purposes of understanding and implementing the invention. This also applies essentially to the technology for the production of the stents according to the invention. As already stated, in general terms, these adopt the appearance of bodies with tubular envelopes having walls with openings. With regard to the production methods, according to the prior art, at least three basic solutions may be used, that is:

forming the stent from a continuous tubular blank to be cut up into individual stents, the walls with openings being formed by techniques such as laser cutting, photo-engraving, electron-discharge machining, etc.;

producing the stent from a strip-like body in which the regions with openings are formed, for example, by the techniques mentioned above, with a view to the subsequent closure of the strip-like element to form a tube, and producing the stent from a metal wire shaped by the successive connection of loops of wire, for example, by means of micro-welding, brazing, gluing, crimping operations, etc.

The first solution described is that which is currently preferred by the Applicant for producing stents according to the embodiments described below, with the exception of the solution to which FIG. 4 relates which intrinsically involves the use of a metal wire. In particular, laser-beam cutting has been found the most flexible solution with regard to the ability to modify the characteristics of the stents quickly during production according to specific requirements of use.

In any case, it is stressed, that this production aspect is of only marginal importance for the purposes of the implementation of the invention in the terms which will be recited further below, particularly with reference to FIG. 4. This also applies with regard to the selection of the individual techniques and of the order in which the various steps described (the production of the walls with openings, parting, any bending of the strip-like element, etc.) are carried out.

In all of the embodiments described herein, the body of the stent 1 extends in a longitudinal direction generally identified by an axis z. For clarity, it should however be pointed out that the stent is intended to be bent, possibly significantly, during use, easy flexibility actually being one of the characteristics sought.

In all of the embodiments described herein, the body of the stent 1 comprises a series of successive, generally annular segments, indicated as 2 in the drawings. As can easily be seen, the stent 1 of FIGS. 1 and 2 comprises seven of these segments, whereas the stent of FIGS. 7 and 8 comprises six.

By way of indication, although this should not be interpreted as limiting of the scope of the invention, the length of the segments 2 measured longitudinally of the stent 1, and hence along the axis z, is of the order of about 2 mm. In other words, for reasons which will become clearer from the following, the segments 2 are quite "short" lengthwise.

As can be appreciated best in the side view of FIG. 2, the various segments of the stent 1 shown therein are connected to one another by pairs of bridges 3, 4 (actually constituting integral parts of the stent wall, as will be explained further below, for example, with reference to FIG. 3) the essential characteristic of which (this applies both to the stent of FIGS. 1 and 2 and to the stent of FIGS. 7 and 8) is to articulate the segments 2 connected respectively thereby in an alternating sequence about mutually perpendicular flexing or bending axes.

This type of solution achieves two advantages.

In the first place, the longitudinal flexibility of the stent 1 which is necessary to facilitate its location at the implantation site, is demanded essentially of the bridges 3, 4, whereas the structural strength and hence the support for the lumen is demanded of the actual structures of the segments 2; all of this is achieved with a capability to optimize the desired characteristics by precise adaptation of the sections of the various component elements.

In the second place, the arrangement of the bridges in a sequence (usually, but not necessarily, alternating), in combination with the fact that, as stated, the segments 2 are quite short, enables a bend to be formed easily, in practice, at any point along the length of the stent 1 in any direction in space, and with very small radii of curvature.

This concept can be understood more easily with reference to the solution of FIGS. 1 and 2 (as will be explained, the same also applies to the solution according to FIGS. 7 and 8) if it is noted that, by virtue of their arrangement at 180° in diametrally opposed positions on the wall of the stent 1, the bridges 3 allow the stent 1 to bend locally about a respective axis x generally transverse the axis z.

The bridges 4, which are also arranged at 180° to one another in a plane perpendicular to that of the bridges 3, allow the stent 1 to bend locally about a second axis y transverse the longitudinal axis z and, in the embodiment shown, perpendicular to the above-mentioned axis x.

Since, as already stated, the segments 2 are quite short, the aforesaid axes x and y are arranged in close proximity to one another in alternating sequence along the length of the stent 1, however many segments 2 there may be.

As a result, the stent can easily be bent, in practically any longitudinal position of the stent 1, about a generic axis d which can be defined on the basis of an equation such as $$\vec{d} = a\vec{x} + b\vec{y} \quad (1)$$

that is, as a linear combination of the bending movements about the axes identified by the vectors $\vec{x}$ and $\vec{y}$.

With reference to the general theory of vectorial spaces, it can also easily be understood that the availability of respective capabilities for bending along two perpendicular axes in sequence, preferably in alternating sequence, constitutes the simplest solution for achieving the desired object. Solutions in which successive segments 2 of the stent 1 are connected by bridges such as the bridges 3 and 4 (or by elements which provide for similar bending capabilities, as will be explained further below with reference to FIGS. 7 and 8) in the region of axes which are not mutually perpendicular would however, at least in principle, be possible. A solution in which, for example, pairs of diametrally-opposed bridges arranged in sequence and spaced apart angularly by 60° may be mentioned by way of example.

Moreover, the alternating sequence described above, that is: axis x, axis y, axis x, axis y may, at least in principle, be replaced by a different sequence, for example, axis x, axis x, axis y, axis y, axis x, axis x, etc. Provision for a capability to bend about the axis x in two adjacent segments 2 followed by a capability to bend about the axis y repeated for two adjacent segments 2, as in the latter example mentioned may, in fact, be advantageous in applications in which an ability to achieve very small radii of curvature is to be given preference.

Figure 7:
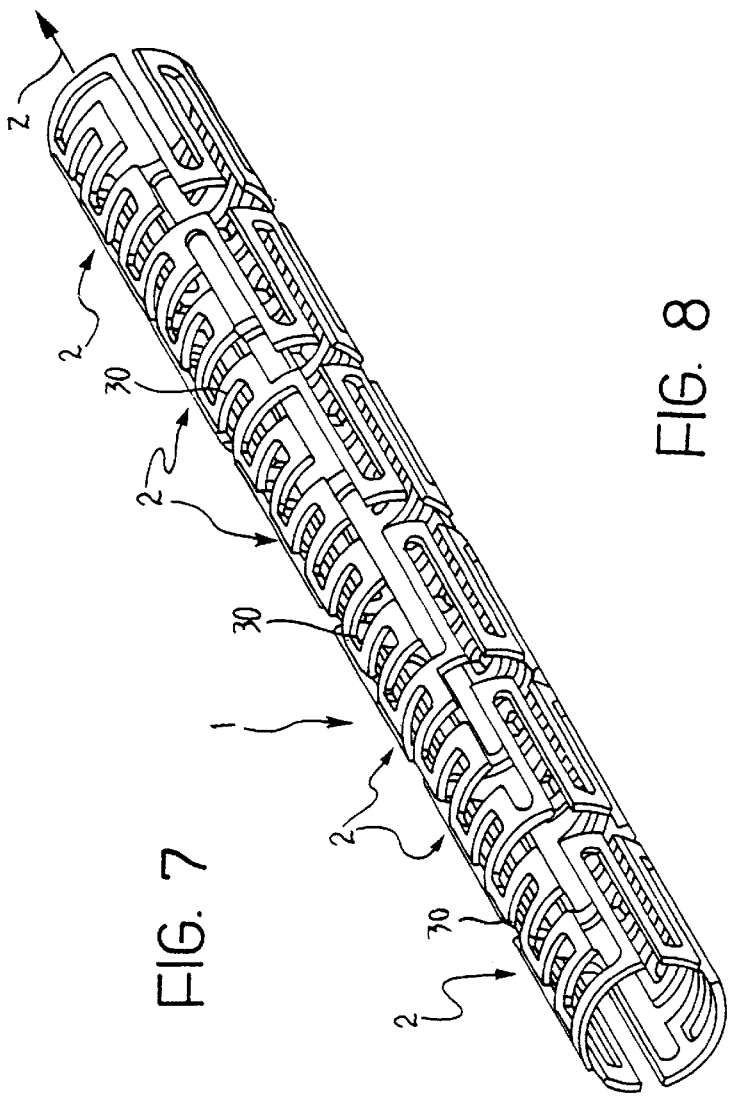
FIG. 7 is a perspective view of another angioplasty stent.
Figure 8:
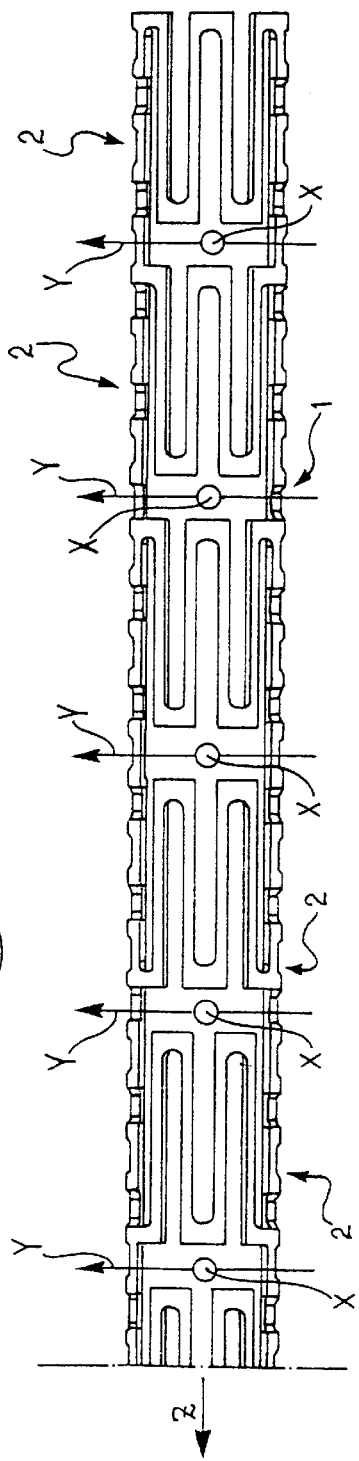
FIG. 8 is a side view of the stent of FIG. 7.

In the solution of FIGS. 7 and 8, the same conceptual solution is achieved in a slightly different manner.

In the solution shown in FIGS. 7 and 8, the various segments 2 are in fact connected to one another by means of bridges forming respective portions of two "spines" of the stent constituted by integral parts of the stent 1 which extend along a generally winding path along two generatrices of the imaginary cylindrical surface of the stent in diametrally opposed positions. The respective structural details will become clearer from the description given below.

Figure 2:
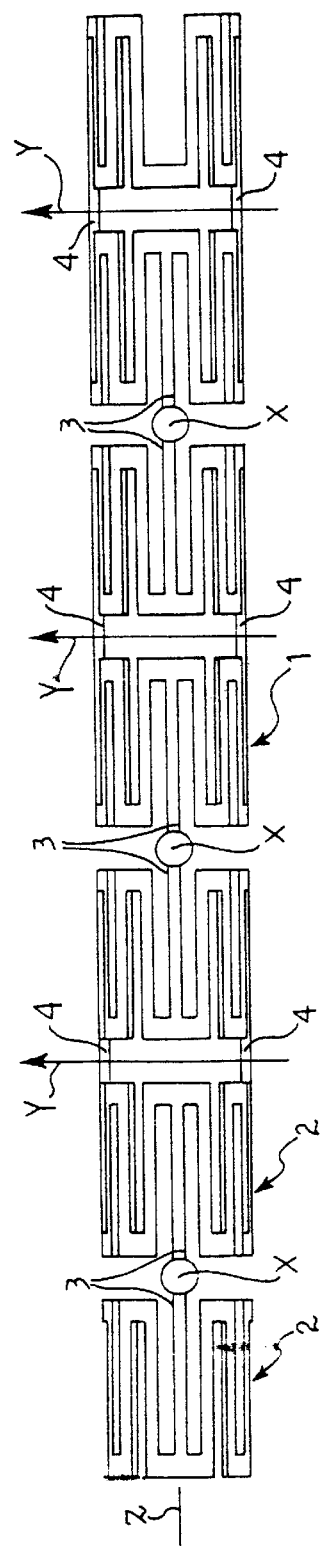
FIG. 2 is a side view of the stent of FIG. 1, on a slightly enlarged scale.

From an observation, in particular, of FIG. 8 and with the use of the same conventions as were used with reference to FIG. 2, it can be seen that the flexibility in the region of respective loops extending between successive segments 2 provided for by the spines 30 achieves the local flexibility about the axis y relative to the general direction defined by the axis z.

The local extensibility of the aforementioned bridges and, in particular, the ability of one of the bridges to extend while the diametrally-opposed bridge retains approximately corresponding longitudinal dimensions, or extends to a more limited extent, or possibly contracts slightly longitudinally, enables the bending movement about the axis x to be achieved, as indicated schematically by a broken line for the segment 2 which is farthest to the left in FIG. 8.

In this embodiment, the stent 2 can thus also be bent in the location of each connection between adjacent segments 2 about a generic axis d defined by an equation such as equation (I) introduced above.

As will be appreciated once again, all of this is achieved while the structure of the individual segments 2 remains substantially unchanged and thus in a manner such that the longitudinal bending of the stent 1 can be attributed essentially to the bending and/or, in general, to the local deformation, solely of the bridges connecting adjacent segments 2.

Figure 3:
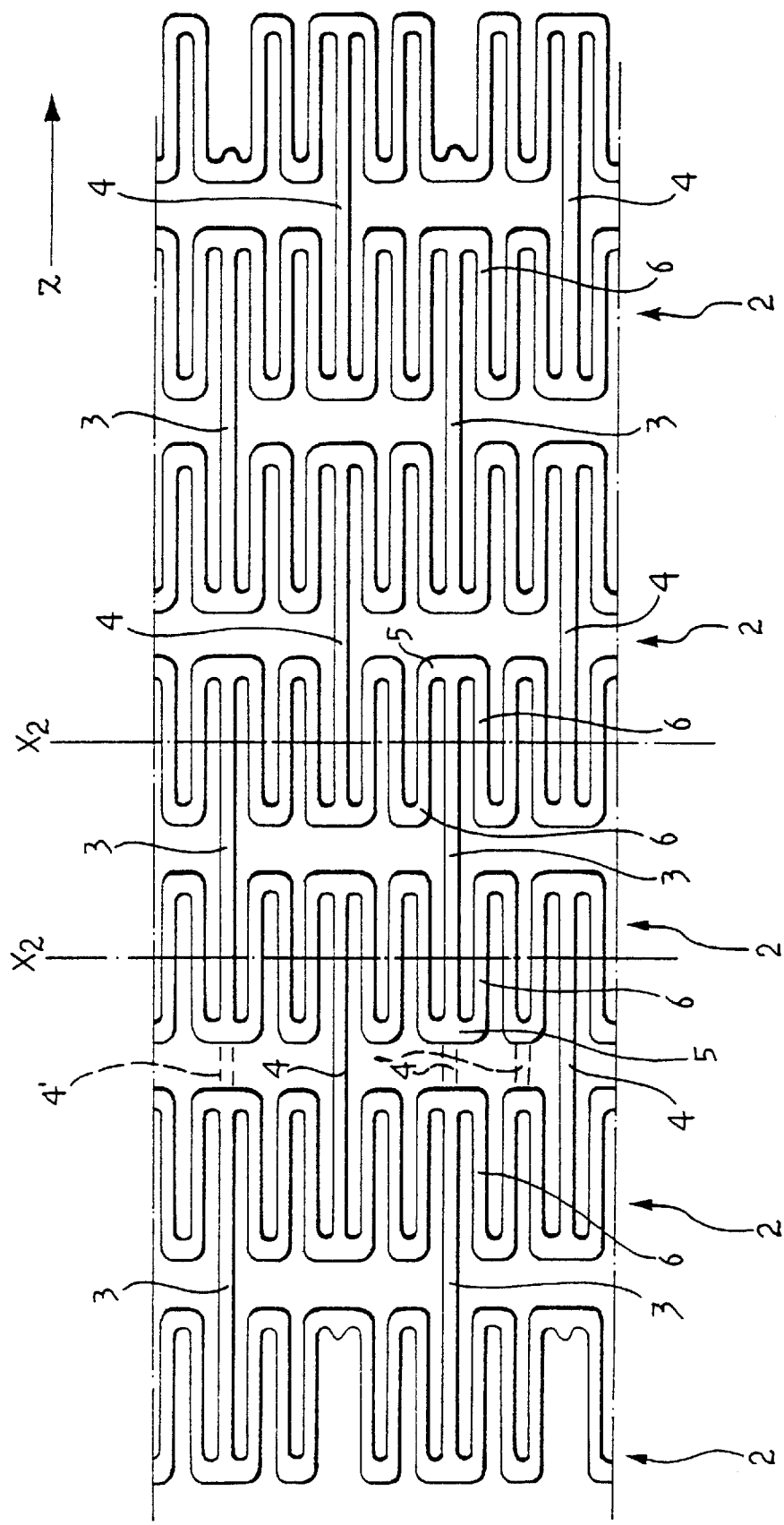
FIG. 3 shows the geometrical characteristics of the wall of the stent of FIGS. 1 and 2 in an imaginary development in a plane, FIG. 4, which is generally comparable to FIG. 3, shows a first variant of the stent generally similar to that shown in FIGS. 1 and 2, FIGS. 5 and 6 are two sections taken on the lines V—V and VI—VI of FIG. 4, respectively.

With reference to FIG. 3, it can be seen that, as already indicated above, this constitutes an imaginary development in a plane, reproduced on an enlarged scale, of the wall of the stent of FIGS. 1 and 2.

In fact, the seven segments 2 connected in alternating sequence by the pairs of bridges 3 and 4 arranged in pairs of diametrally-opposed elements disposed at 90° in alternating sequence can be seen in FIG. 3. As already stated, this is an imaginary development in a plane which may correspond to the development of a strip-like blank from which the stent 1 is then produced by bending of the blank to form a tube.

It can also be noted from an observation of FIG. 3 that the generally annular body of each segment 2 comprises in the embodiments shown, a set of approximately sinusoidal loops of substantially uniform size (measured circumferentially relative to the element 2) which is doubled in the region of the loops from which the bridges 3, 4 extend, in the manner explained further below.

It is possible to recognise, within each segment 2, a respective imaginary median plane X2 which, in the embodiments illustrated, is generally perpendicular to the longitudinal axis z. Two of these planes, indicated X2 are shown in FIG. 3 (and in FIG. 9); naturally, since these are developments in a plane, the median planes in question are represented in the drawings by straight lines.

It can thus be noted that each segment 2 comprises a sequence of loops, each loop (approximately comparable to half of a sinusoidal wave) defining a respective concave portion 5, the concave side of which faces towards the median plane X2, and which is connected to two approximately straight arms 6.

By way of indication, only two of these loops interconnected by a bridge 3 have been marked specifically in FIG. 3. In particular, these are the two loops of which the concave portions are indicated 5 and the lateral arms are indicated 6.

It can easily be understood that the radial expansion of the stent 1 takes place substantially as a result of an opening-out of the aforementioned loops; by way of indication, with reference to the development in a plane of FIG. 3, the radial expansion of the stent corresponds to a stretching of the development in a plane shown in FIG. 3 in the sense of an increase in height and hence a vertical expansion of FIG. 3.

In practice, this radial expansion corresponds to an opening-out of the concave portions 5, whereas the lateral arms 6 of each loop remain substantially straight.

The localization of the plastic deformation of the stent 2 in the concave portions of the loops 5 may be favored (as will be explained further below with reference to FIG. 4) by means of the cross-sections and/or the cross-sectional areas of the portions of each loop.

In any case, the radial expansion (vertical stretching of the development in a plane of FIG. 3) affects essentially the concave portions 5 of the loops of the elements 2 and in no way affects the bridges 3, 4 which extend longitudinally (axis z).

It will be appreciated that the same also applies to the solution shown in FIG. 4 (which will be referred to further below) in which one of the median planes X2 has been shown, only one of the loops being indicated and its concave portion 5 and its lateral arms 6 being identified specifically. The same criterion also applies to the solution of FIGS. 7 and 8; in this connection, reference should be made to the development in a plane of FIG. 9. In this drawing, as in FIG. 3, two median planes X2 of two segments 2 have been indicated, and the concave portion 5 and the lateral arms 6 of two opposed loops, between which a portion of one of the sinusoidal spines 30 extends like a bridge, are also shown.

Figure 4:
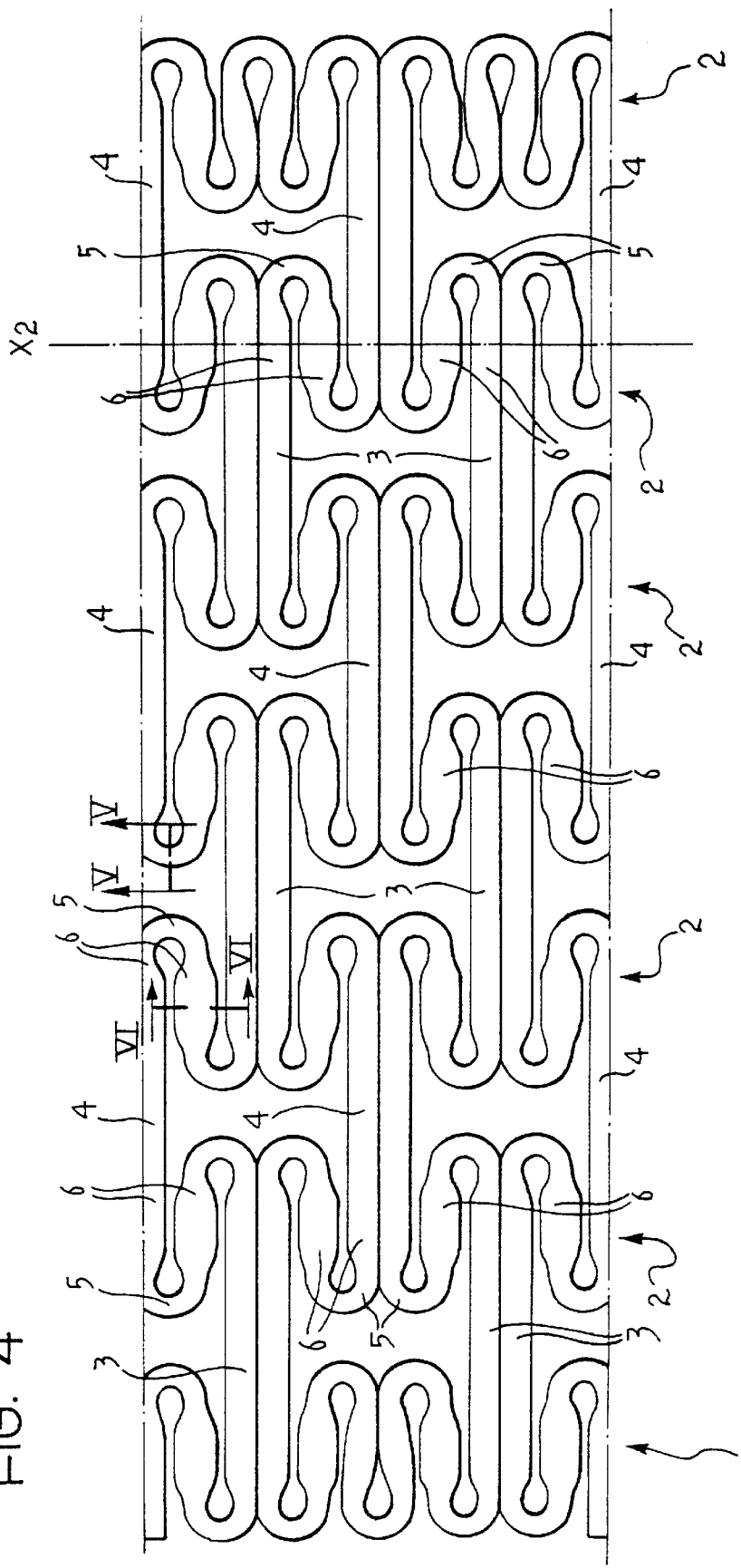
Figure 9:
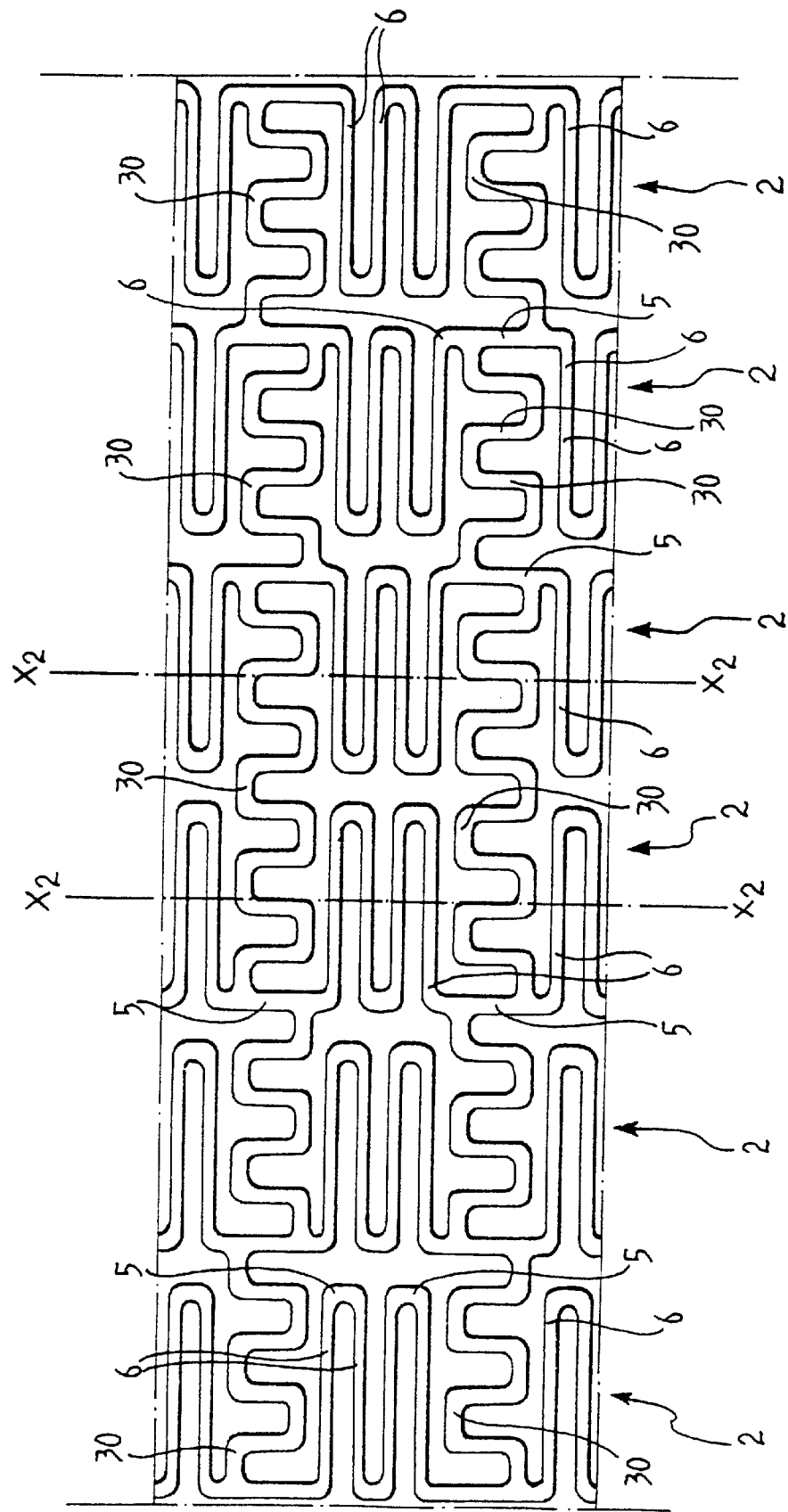
FIG. 9 shows essentially in the same manner as FIG. 3, an imaginary development in a plane of the wall of the stent of FIGS. 7 and 8, and FIGS. 10 and 11 show further possible developments of the invention.

As can be seen best from a comparison of FIGS. 3, 4 and 9, a feature common to all of the solutions described is that the radial expansion of the segments 2 corresponds, within each segment 2, to an imaginary movement of the concave portion 5 of each loop towards the median plane X2 of the segment 2 of which this loop forms part.

Anyone reading this description can easily perceive this, for example, by thinking of the segment 2 corresponding to the plane X2 farthest to the right in FIG. 3 as extending vertically. As a result of this stretching, carried out precisely along the line X2 which identifies the aforesaid plane, the concave portion 5 of the loop indicated in fact moves towards the line X2, the same behaviour being followed, in opposite directions, according to their different locations relative to the line X2, by the concave portions of all of the other loops.

If, with reference to the bridges 3 (and the same also applies to the bridges 4 as well as to the individual portions of the spines 30 which define the parts equivalent to the bridges 3 and 4 in FIG. 9), it is considered that the connection to the relative segments 2 is formed in the region of the concave (or inside) portion of a respective loop, it can easily be appreciated that the radial expansion of the segments 2 is accompanied, so to speak, by a thrust exerted on the bridges 3, 4 (and on the respective spine portions 30). This thrust corresponds, so to speak, to an expulsion of the bridges or of the spine portions in question from the corresponding segment 2.

To concentrate attention once again on the segment 2 the median plane X2 of which is farthest to the right in FIG. 3, if the segment 2 in question is thought of as being stretched vertically, it will be seen that, as a result of the movement of the concave portions (such as, for example, the concave portion indicated 5 in the segment 2 in question) towards the plane X2, the respective bridges 3 tend to move towards the left relative to the median plane X2 of the corresponding segment 2.

This expulsion effect on the bridges 3 is beneficial for eliminating the tendency demonstrated by many stents of the prior art to contract longitudinally during radial expansion.

By the adoption of a geometry such as that shown in FIGS. 3 and 4, for example, the axial contraction of the segments 2 resulting from their radial expansion is in fact compensated (and possibly even overcome) by the above-described "expulsion" of the bridges 3 and 4. Tests carried out by the Applicant show, in this connection, that, a geometry, for example, such as that illustrated in FIGS. 3 and 4 causes the stent 1 not only not to shorten but, on the contrary, to lengthen slightly during the radial expansion.

The explanation of this mechanism is quite simple. In this connection, it suffices to consider, again with reference to FIG. 3, what would happen if, theoretically, instead of being located where they are shown (and thus connecting respective concave loop portions of adjacent segments 2), the bridges 4 of two aligned loops of two adjacent segments 2 were arranged as indicated by broken lines and indicated 4' and hence not connecting concave (inside) loop portions but connecting convex (or outside) loop portions.

The bridges 4' indicated above are extremely short (it will be remembered, by way of reference, that the axial length of the segments 2 may be of the order of 2 mm). Even during radial expansion, the concave portions (and consequently the convex portions) of all of the loops of each segment in any case retain their alignment with a plane parallel to the median plane X2 at each end of each segment 2. This alignment is thus also retained by the concave or convex portions connected between two adjacent segments 2 by the same bridge 3, the length of which is not changed during the radial expansion.

Consequently, the length of a stent in which the bridges 3 were arranged as shown in FIG. 3 and the bridges 4 as schematically indicated 4', again in FIG. 3, (naturally with reference to all of the pairs of bridges 4 present in the stent) would remain practically unchanged during radial expansion.

On the other hand, as already stated, with the use of the geometry shown in FIG. 3, owing to the superimposition of the various deformation movements, the axial length of the stent 1 is not merely kept constant but even increases slightly. It will also be understood from the explanation given above that, even though the location of the bridges indicated 4' is mentioned theoretically for explanation, it could actually be used, according to specific requirements. Moreover, it can easily be understood from the foregoing explanation that the conservation of the axial length during the radial expansion does not necessarily require all of the bridge elements (which are not affected by the deformation resulting from the radial expansion) to be connected to concave or inside portions of respective loops of the segments 2. In fact it suffices, for this purpose, for one such connection to be provided for each longitudinal section which is intended to contract longitudinally as a result of the radial expansion of the stent 1.

For example, in the embodiment shown by solid lines in FIG. 3, (the same also applies to the embodiment of FIGS. 4 and 9) each of the segments 2 comprises a section which is intended to contract longitudinally as a result of the radial expansion. A corresponding connection of bridges 3, 4 is therefore provided in each of these segments according to the criteria described above.

With reference, on the other hand, to the connection arrangement of the bridges 4' indicated primarily for didactic purposes in FIG. 3, it can be noted that each set of two segments 2 interconnected by respective bridges 3 constitutes, precisely for the reasons described above, a section of stent which does not contract substantially longitudinally during radial expansion. For this reason, the connection between these sections can take place by means of bridges such as those which are indicated 4' and shown in broken outline in the drawing and which are not connected to a concave (or inside) loop portion.

It can be noted from an examination of the diagram of FIG. 9, that all of the segments 2 illustrated therein can contract axially as a result of radial expansion. For this reason, the bridges defined by the sinusoidal spines 30 and connecting adjacent segments 2 satisfy precisely the condition described above, that is, connection to the concave portion of a respective loop.

With regard to the general geometry, the variant of FIG. 4 again proposes the connection arrangement described above with reference to FIG. 3.

FIG. 4 shows how a stent wall structure having the geometry described with reference to FIG. 3 can also be formed from one or more pieces of wire bent so as to form a set of loops which is substantially similar to that shown in FIG. 3, and in which the bridges 3 and 4 comprise wire portions which are coupled (that is, placed side by side parallel to one another) and connected, for example, by welding or other joining methods (for example, brazing, gluing, crimping, etc.).

Figure 6:
Figure 5:
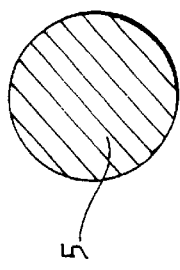

The use of a wire enables different cross-sections and/or cross-sectional areas to be attributed (for example, by a mechanical operation to shape the wire) to the concave portions 5 of the loops and to the straight arms 6 which extend therefrom. For example, it can readily be appreciated that the cross-section of FIG. 5 is in fact the cross section of a concave portion taken in its tip portion, whereas the cross-section of FIG. 6 corresponds to the connection region of two straight arms extending generally longitudinally relative to the stent (axis z).

In particular, in the concave portions of the loops, the wire constituting the stent wall may retain a round cross-section, but in the straight portions 6 may adopt a cross-section which is generally flattened in the plane of the wall (and hence along the imaginary cylindrical envelope) of the stent 1.

This different shaping enables various results to be achieved.

The straight portions 6 are intrinsically more resistant to bending in the plane in which they are generally flattened so that the a force opening out the two arms 6 connected to a common concave portion 5 brings about a deformation of the loop in the concave portion 5. Although the arms 6 are opened out, they retain a generally straight shape; in this connection, it will be noted that the arms which are coupled to form the bridges 3 and 4 nevertheless retain a straight orientation along the longitudinal axis z of the stent 1.

By virtue of their flattened shape the arms 6 expose a wider surface to the wall of the lumen supported by the stent in its radially expanded condition. The wall of the lumen is therefore subjected to a distributed load preventing the formation of concentrated stress regions.

The dimensions of the wire can be optimized in the concave portions 5 in order to achieve optimal characteristics of plastic deformability when the stent is expanded radially and, at the same time, resistance to subsequent stresses which may tend to close up the stent 1.

It should in any case be pointed out, for clarity, that the solution of making the cross-sections and/or the cross-sectional areas of the various parts of the stent wall different in the terms illustrated by way of example with reference to FIG. 4 is also practicable in the solutions described with reference to FIGS. 3 and 9, (although with technological solutions other than the mechanical squashing of the wire mentioned with reference to FIG. 4).

To examine this latter solution, and with further reference to the perspective and elevational views of FIGS. 7 and 8, it can be noted that, as a general rule, the structure and shape of the loops constituting the various segments 2 is generally similar to that described above with reference to FIGS. 3 and 4. In particular, as indicated in the segment 2 situated farthest to the left, it is also possible generally to distinguish in the loops shown in FIG. 9 a concave (or inside) portion 5, extending from which are two straight arms 6 which are intended to be opened out when the stent 1 is expanded radially.

The wall structure of FIG. 9 differs from that shown in FIGS. 3 and 4 essentially in that the bridges which interconnect the various segments 2 comprise the two spines 30 extending with a generally sinusoidal shape along two diametrally opposed generatrices of the structure of the stent 1.

Naturally, the presence of two of these spines does not constitute an essential choice. For example, instead of having two spines 30 which are diametrally opposed (and hence spaced apart angularly by 180°) it is possible to use a single spine of this type or three spines spaced angularly by 120° etc.

In any case a structure with spines of the type described can also implement an equation such as equation (I) given above, for the purposes of the longitudinal bending of the stent 1. The difference in comparison with the embodiment shown in FIGS. 1 to 4 lies in the fact that, in this first solution, the axes x and y in fact correspond to the axes about which the bending of the pairs of bridges 3, 4 can take place. In the embodiment of FIGS. 7 to 9, on the other hand, (in this connection see also the elevational view of FIG. 8), each section of the spine 30 extending to connect two adjacent segments 2 can express two possibilities for relative orientation between the two segments 2 connected, that is:

twisting or, more correctly, bending in the general plane of the spine 30, and extension, or in general, variation in length in this plane.

This concept may become clearer to experts in mechanics if it is noted that, in practice, both the solution illustrated in FIGS. 1 to 4 and the solution illustrated in FIGS. 7 to 9 form structures generally comparable to that of a universal joint.

The generally sinusoidal shape of the two spines 30 enables the longitudinal extensibility of the spines to be utilised for bending purposes without giving rise to stresses which are oriented tangentially relative to the wall of the stent and hence risk giving rise to undesired twisting. It will, in any case, be appreciated that the length of the stent of FIGS. 7 to 9 (that is, its extent along the axis z) can change entirely independently of the radial expansion of the segments 2. This can easily be seen if it is noted that the overall shape of the spines 30 is sinusoidal and, even where they are connected to concave portions of respective loops (see in particular the portion of the spine 30 which is shown in the lower portion of FIG. 9 connecting the two elements 2 of which the median planes X2 are indicated) the connection with these concave portions 5 does not change the general sinusoidal shape of the spine in question. In other words, the spine 30 is connected to the outer edge of the outside of the concave portion 5 on one side or wall thereof and continues from the inside of the concave portion, from the opposite side or wall.

The solution described provides for the entire body 1 of the stent, or at least part of it, to comprise a substantially reticular structure, the branches of which (in the embodiment shown, the annular walls of the segments 2 and the two spines 30) define geometrical figures which can be identified as fractals.

The term "fractal", coined by the mathematician B. Mandelbrot in 1975, indicates in general a geometrical figure which has internal symmetries to whatever scale it is enlarged, and which is produced as a limit configuration of a succession of fragmentary curves from each of which the next is obtained on the basis of an assigned rule, for example, by replacing each side with a predetermined fragmentary, so-called generative or generator line.

Solutions such as those shown by way of example in FIGS. 2, 7 and 9 can be developed with the use of higher-order fractals, as shown schematically in FIGS. 10 and 11.

In particular, FIG. 10 shows, by way of example, the use of higher-order fractals to produce segments 2, and FIG. 11 shows, by way of example, the use of higher-order fractals to produce the spine or spines 30. Clearly the solutions shown by way of example may be combined, in the sense that the higher-order fractals may be used both for the segments 2 and for the spines 30.

In any case, the use of fractal geometry has been found advantageous since it enables the performance and/or the mechanical characteristics of the various portions of the wall of the stent 1 to be optimized with regard to the specific stresses to which it has to respond in use.

What is claimed is:

1. A stent for supporting the wall of a vessel comprising a tubular body having at least two annular segments interconnected by a plurality of connectors, the tubular body having a wall including an inner wall surface and an outer wall surface defining a wall thickness therebetween, the tubular body further having a plurality of openings between the inner wall surface and the outer wall surface, the tubular body being expandable from a radially contracted condition to a radially expanded condition, at least one annular segment being configured such that a first portion of the at least one annular segment has a first outer wall surface width and a second portion of the at least one annular segment has a second outer wall surface width, the first outer wall surface width being greater than the second outer wall surface width such that the outer wall surface of the first portion of the at least one annular segment is configured to provide greater support to the wall of the vessel than the outer wall surface of the second portion of the at least one annular segment.

2. The stent of claim 1 wherein the tubular body is formed from a tubular blank and further wherein the plurality of openings is formed from one of laser cutting, photo-engraving, or machining.

3. The stent of claim 1 wherein the tubular body is formed from a strip-like element closed to form a tube and further wherein the plurality of openings is formed from one of laser cutting, photo-engraving, or machining.

4. The stent of claim 1 wherein the tubular body is formed from a metal wire.

5. A stent comprising a tubular body having a wall including an inner wall surface and an outer wall surface defining a wall thickness therebetween, the tubular body further having a plurality of openings between the inner wall surface and the outer wall surface, the tubular body being expandable from a radially contracted condition to a radially expanded condition, the tubular body having a plurality of annular segments, each annular segment connected to at least one other annular segment by a bridge portion, the tubular body being configured such that a first portion of at least one annular segment has a first wall thickness and a first outer wall surface width and a second portion of the at least one annular segment has a second wall thickness and a second outer wall surface width, the first wall thickness being greater than the second wall thickness, the first and second wall thicknesses being selected in order to enhance at least one characteristic of the tubular body selected from plastic deformability, resistance to bending, and resistance to the formation of concentrated stress regions along the wall of the vessel when the tubular body is expanded, the outer wall surface of the tubular body being configured such that the outer wall surface of the first portion of the at least one annular segment provides greater support to the wall of the vessel than the outer wall surface of the second portion of the at least one annular segment.

6. The stent of claim 5 wherein the tubular body is formed from a tubular blank and further wherein the plurality of openings is formed from one of laser cutting, photo-engraving, or machining.

7. The stent of claim 5 wherein the tubular body is formed from a strip-like element closed to form a tube and further wherein the plurality of openings is formed from one of laser cutting, photo-engraving, or machining.

8. The stent of claim 5 wherein the tubular body is formed from a metal wire.

9. The stent of claim 1 wherein the annular segments have a substantially sinusoidal shape comprising a plurality of peaks connected by a plurality of arm sections and wherein the second portion includes a peak and the first portion includes at least a part of an arm section.

10. The stent of claim 1 wherein the annular segments comprise a plurality of alternating peaks connected by arm sections to form a wave-shaped pattern and wherein the second portion includes a peak and the first portion includes at least one part of an arm section.

11. The stent of claim 9 wherein the second portion includes each of the peaks and the first portion includes at least a part of each arm section.

12. The stent of claim 10 wherein the second portion includes each of the peaks and the first portion includes at least a part of each arm section.

13. A stent for supporting the wall of a vessel comprising a tubular body having at least two annular segments interconnected by a plurality of connectors, the tubular body having a wall including an inner wall surface and an outer wall surface defining a wall thickness therebetween, the tubular body farther having a plurality of openings between the inner wall surface and the outer wall surface, the tubular body being expandable from a radially contracted condition to a radially expanded condition, at least one annular segment being configured such that a first portion of the at least one annular segment has a first outer wall surface width and a first wall thickness and a second portion of the at least one annular segment has a second outer wall surface width and a second wall thickness, the first outer wall surface width being greater than the second outer wall surface width and the first wall thickness being less than the second wall thickness such that the outer wall surface of the first portion of the at least one annular segment provides greater support to the wall of the vessel than the outer wall surface of the second portion of the at least one annular segment.

14. The stent of claim 13 wherein the first portion has a first cross-sectional area defined by a first plane perpendicular to a longitudinal axis of the tubular body and intersecting the first portion and the second portion has a second cross-sectional area defined by a second plane perpendicular to a longitudinal axis of the tubular body and intersecting the second portion, the first cross-sectional area being substantially equal to the second cross-sectional area.

15. The stent of claim 13 wherein the tubular body is formed from a tubular blank and further wherein the plurality of openings is formed from one of laser cutting, photo-engraving, electron-discharge, or machining.

16. The stent of claim 13 wherein the tubular body is formed from a stip-like element closed to form a tube and further wherein the plurality of openings is formed from one of laser cutting, photo-engraving, electron-discharge, or machining.

17. The stent of claim 13 wherein the tubular body is formed from a metal wire.

18. The stent of claim 13 wherein the annular segments have a substantially sinusoidal shape comprising a plurality of peaks connected by a plurality of arm sections and wherein the second portion includes a peak and the first portion includes at least a part of an arm section.

19. The stent of claim 13 wherein the annular segments comprise a plurality of alternating peaks connected by arm sections to form a wave-shaped pattern and wherein the second portion includes a peak and the first portion includes at least one part of an arm section.

20. The stent of claim 18 wherein the second portion includes each of the peaks and the first portion includes at least a part of each arm section.

21. The stent of claim 19 wherein the second portion includes each of the peaks and the first portion includes at least a part of each arm section.

* * * * *